US00PP35028P2

(12) United States Plant Patent
White

(10) Patent No.: US PP35,028 P2
(45) Date of Patent: Mar. 14, 2023

(54) APPLE TREE NAMED 'PREMA025'

(50) Latin Name: *Malus domestica*
Varietal Denomination: PremA025

(71) Applicant: Prevar Limited, Hastings (NZ)

(72) Inventor: Allan G. White, Hastings (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 17/803,709

(22) Filed: Oct. 21, 2022

(51) Int. Cl.
*A01H 6/74* (2018.01)
*A01H 5/08* (2018.01)

(52) U.S. Cl.
USPC ..... Plt./161
CPC ..... *A01H 6/7418* (2018.05)

(58) Field of Classification Search
USPC ..... Plt./156, 161
See application file for complete search history.

*Primary Examiner* — Karen M Redden
(74) *Attorney, Agent, or Firm* — Michelle Bos Legal LLC

(57) ABSTRACT

A new and distinct apple tree named 'PremA025', notable for its resistance to apple scab and for its fruit, which has an attractive red skin color, excellent texture and sweet rich flavor.

3 Drawing Sheets

Latin name: *Malus domestica.*
Variety denomination: PremA025.

BACKGROUND OF THE VARIETY

The new apple tree 'PremA025' was created in the course of a planned breeding program carried out at Havelock North, New Zealand. 'PremA025' originated from a controlled cross made in 1997 of 'Sciros' (seed parent, U.S. Plant Pat. No. 7,814) and 'Pinkie' (pollen parent, not patented). 'PremA025' was selected from a population of seedlings derived from the parents, and was singled out for further observation for its resistance to apple scab, and for its fruit, which has an attractive red skin color, excellent texture and sweet rich flavor. The variety was first asexually propagated by grafting at Havelock North, New Zealand in 2004. 'PremA025' trees have been observed over a number of asexually propagated generations, and have been found to remain true to type.

'PremA025' is distinguished from parent varieties 'Sciros' and 'Pinkie' and from similar variety 'Braeburn' (not patented) as set forth in the tables below.

TABLE 1

Comparison of 'PremA025' to 'Sciros'

| Characteristic | 'PremA025' | 'Sciros' |
|---|---|---|
| Fruit size | 225 g | 275 g |
| Leaf color | Green 137B | Green 134A |

TABLE 2

Comparison of 'PremA025' to 'Pinkie'

| Characteristic | 'PremA025' | 'Pinkie' |
|---|---|---|
| Skin color | Red solid flush | Pink blush on yellow background |
| Tree habit | Upright-spreading | Upright |

TABLE 3

Comparison of 'PremA025' to 'Braeburn'

| Characteristic | 'PremA025' | 'Braeburn' |
|---|---|---|
| Fruit shape | Globose | Ovoid |

BRIEF DESCRIPTION OF THE PHOTOGRAPHS

The attached photographs of 6-year-old 'PremA25' trees and their flowers and fruit were taken at Wapato, Wash. during 2022 growing season. The trees were grown on seedling (*Malus domestica*) rootstock.

DETAILED BOTANICAL DESCRIPTION OF THE VARIETY

Figure 1:
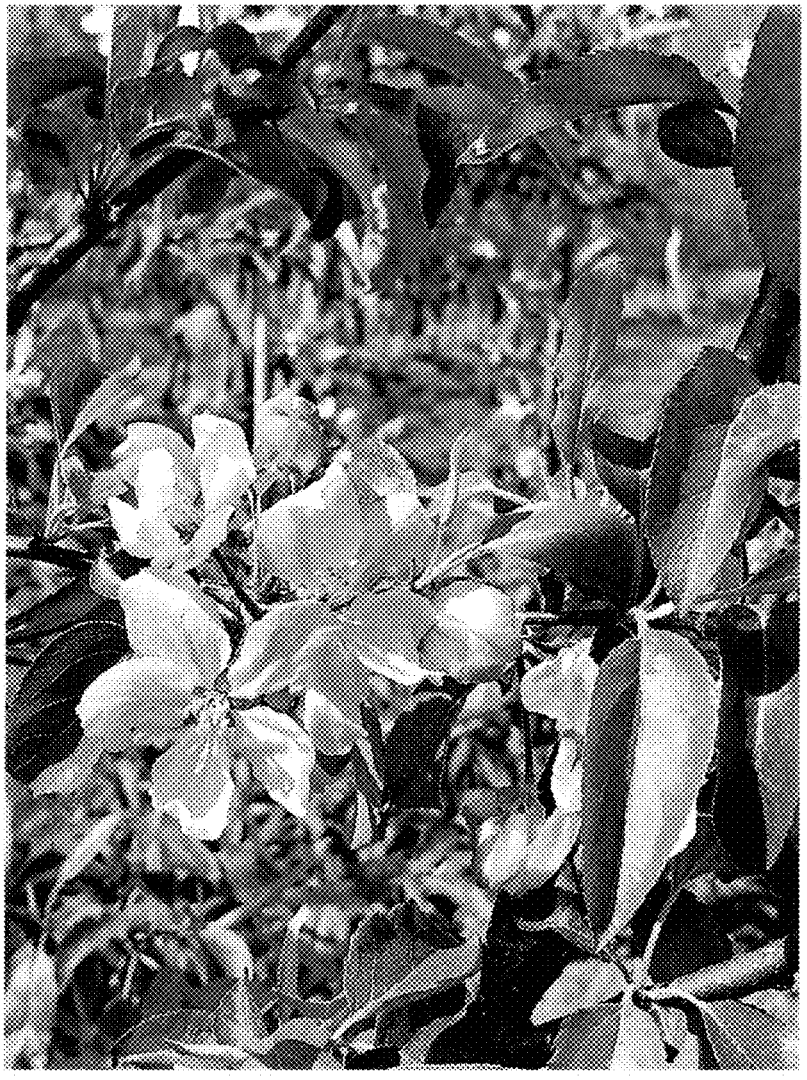
FIG. 1 shows blossoms and leaves on a 'PremA025' apple tree.
Figure 2:
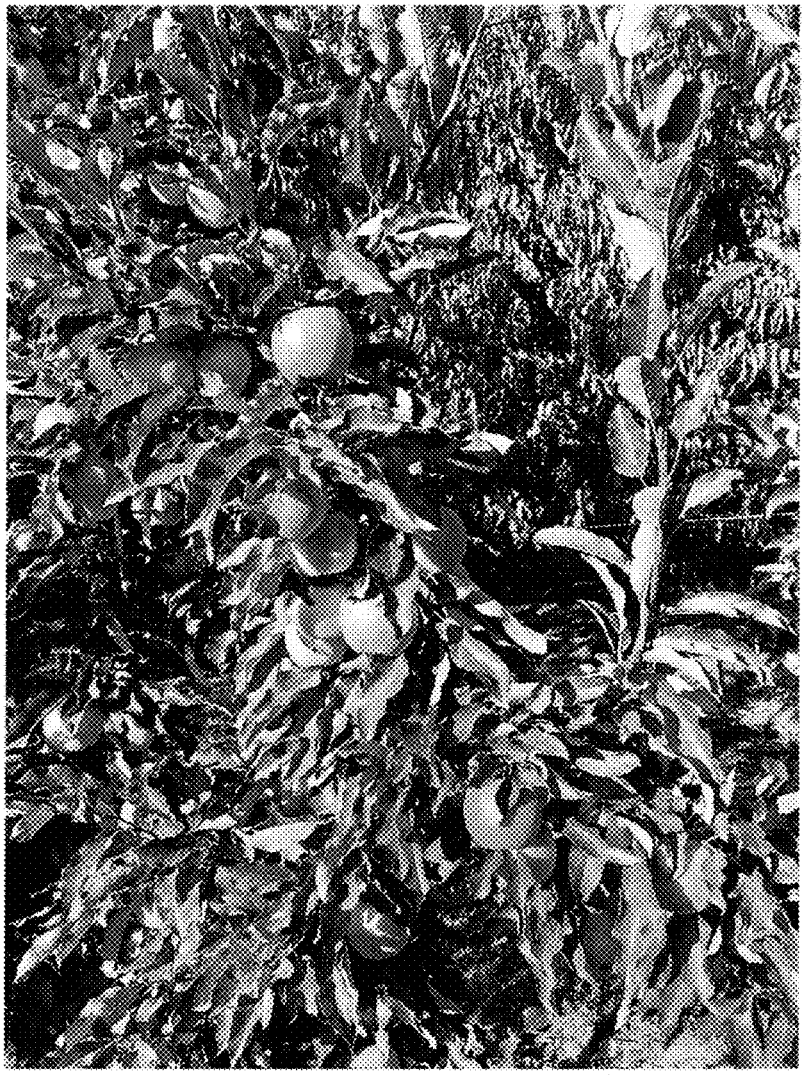
FIG. 2 shows the fruit, branches and leaves of a 'PremA025' apple tree; and, FIG. 3 shows fruit and leaves on a 'PremA025' apple tree.
Figure 3:
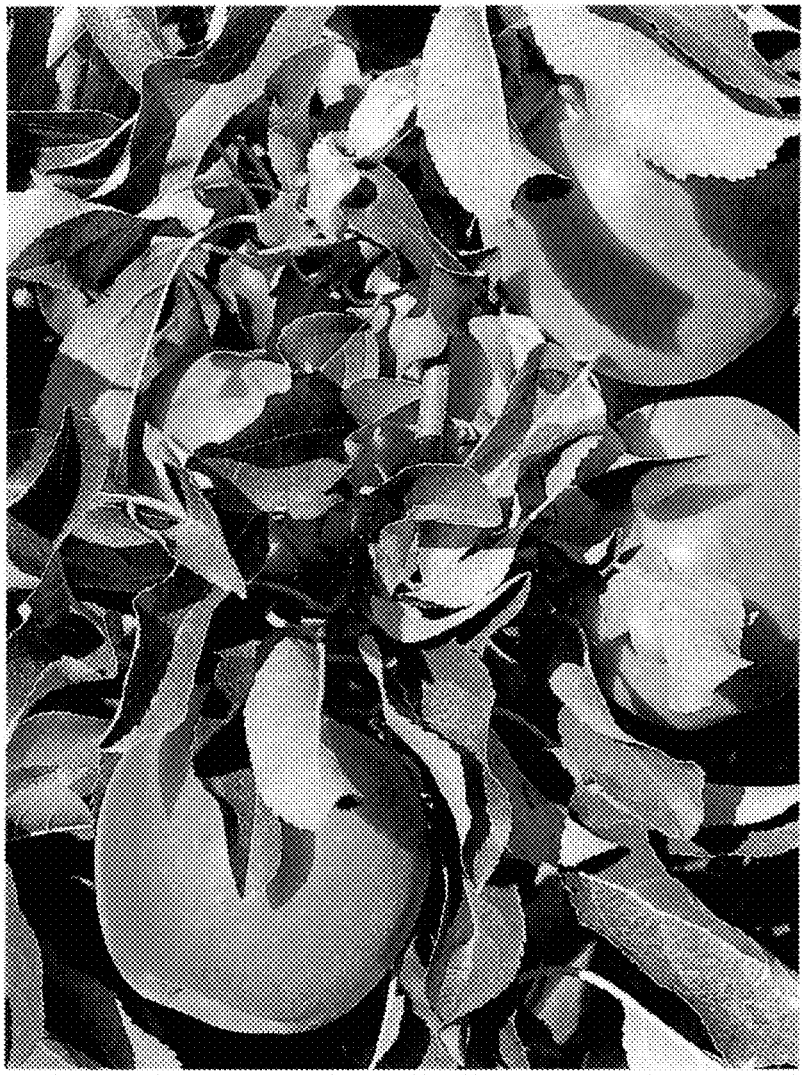

The following-detailed botanical description is based on observations of 6-year-old trees during the 2022 growing season at Wapato, Wash. The described trees were grown on seedling (*Malus domestica*) rootstock. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, 4$^{th}$ ed. (Royal Horticultural Society, 2001).

Tree:

*Vigor.*—Moderate.
*Type.*—Ramified.
*Habit.*—Semi-upright.

*Height*.—3.7 meters.
*Spread*.—1.2 meters to 1.5 meters.
*Trunk diameter* (*at* 30 *cm above the graft*).—5 cm.
*Bearing*.—On spurs.
*Bark texture*.—Rough.
*Bark color*.—Greyed-orange N167A.
*Lenticel length*.—5 mm.
*Lenticel width*.—1 mm.
*Lenticel color*.—White NN155B.
*Lenticel density*.—7 per 10 $cm^2$.

Branch (fruiting branches located at around 1 m above the graft union):
*Length*.—55 cm.
*Diameter*.—6 mm.
*Crotch angle*.—70°.
*Bark color*.—Greyed-orange 177B.
*Branch lenticel length*.—2 mm.
*Branch lenticel width*.—1 mm.
*Branch lenticel shape*.—Rectangular.
*Branch lenticel color*.—White 155B.
*Branch lenticel density*.—8 to 10 per $cm^2$.

One year old shoot:
*Length*.—26 cm.
*Diameter*.—4 mm.
*Color*.—Greyed-orange 177B.
*Pubescence*.—Present.
*Internode length*.—3 cm to 4 cm.
*Shoot lenticel length*.—1 mm.
*Shoot lenticel width*.—0.5 mm.
*Shoot lenticel shape*.—Rectangular.
*Shoot lenticel color*.—White 155B.
*Shoot lenticel density*.—6 to 8 per $cm^2$.

Flower buds:
*Stage described*.—Tight.
*Quantity per spur*.—5.
*Bud shape*.—Oval.
*Apex shape*.—Rounded.
*Length*.—1 cm.
*Diameter*.—0.5 cm.
*Color*.—Red-purple 67A with white N155B toward base.

Flowers:
*Diameter of fully open flower*.—45 mm.
*Relative position of petal margins*.—Overlapping.
*Date of first bloom*.—Apr. 21 (2022).
*Date of full bloom*.—Apr. 27 (2022).
*Pollination requirement*.—Pollinator required.

Petals:
*Number per flower*.—5.
*Petal shape*.—Oval.
*Length*.—2 cm.
*Width*.—1.3 cm.
*Apex shape*.—Obtuse.
*Base shape*.—Cuneate.
*Margin*.—Entire, ruffled.
*Color of upper surface*.—White NN155C with red-purple 59D near base.
*Color of lower surface*.—White NN155C with purple 75B near base.

Pistils:
*Length*.—1.2 cm.
*Color*.—Yellow-green 145B.

Stigma:
*Diameter*.—1 mm.
*Color*.—Yellow-green 145C.

Stamens:
*Quantity*.—15 to 20.
*Length*.—10 mm.
*Anther color*.—Yellow 2B.
*Pollen*.—Scarce.
*Pollen color*.—Yellow 2B.

Pedicel:
*Length*.—3 cm.
*Diameter*.—1 mm.
*Color*.—Yellow-green 147D.

Sepals:
*Quantity*.—5.
*Color*.—Yellow-green 146D.
*Shape*.—Lanceolate.
*Apex shape*.—Aristulate.
*Margin*.—Entire.

Leaves:
*Shape*.—Ovate.
*Length*.—10 cm.
*Width*.—5 cm.
*Length/width ratio*.—2:1.
*Blade margin*.—Serrate.
*Apex*.—Acuminate.
*Base shape*.—Equilateral.
*Color of upper surface*.—Green NN137C.
*Color of lower surface*.—Green 139C.
*Attitude in relation to shoot*.—Upward.

Petiole:
*Length*.—4 cm.
*Diameter*.—1 mm.
*Color*.—Yellow-green 145C with green NN137C near base.

Fruit:
*Quantity per cluster*.—2 (after thinning).
*Diameter*.—8 cm.
*Height*.—6 cm.
*Weight*.—225 g.
*General shape in profile*.—Flat-globose.
*Position of maximum diameter*.—At equator.
*Ribbing*.—None.
*Crowning at calyx end*.—Slight.
*Size of eye*.—Small.
*Aperture of eye*.—Open.
*Depth of eye basin*.—1.4 cm.
*Width of eye basin*.—2.5 cm.
*Length of sepal*.—6 mm.
*Bloom of skin*.—Present.
*Greasiness of skin*.—Present.
*Background color of skin*.—Yellow-green 150D.
*Amount of over color*.—80%.
*Over color of skin*.—Red 47C to 47D.
*Intensity of over color*.—Moderate.
*Pattern of over color*.—Solid flush.
*Lenticels*.—Pronounced.
*Amount of russet around stalk cavity*.—Abundant.
*Amount of russet on cheeks*.—Absent.
*Area of russet around eye basin*.—Sparse.
*Length of stalk*.—35 mm.
*Thickness of stalk*.—3 mm.
*Depth of stalk cavity*.—2 cm.
*Width of stalk cavity*.—2.5 cm.
*Stalk color*.—Yellow-green 153C.
*Firmness of flesh*.—Firm, 15 lbs.

*Flesh texture*.—Somewhat coarse.

*Juiciness*.—Moderate.

*Brix*.—11° Brix.

*Flesh color*.—White 155B.

Seeds:

*Quantity per fruit*.—13.

*Shape*.—Ovate.

*Length*.—10 mm.

*Width*.—5 mm.

*Color*.—Greyed-orange 166B.

Harvest:

*Time for harvest*.—About Oct. 5 (2022, Wapato, Wash.).

*Number of picks*.—One.

*Disease and pest resistance*.—Resistant to black spot (apple scab, *Venturia inaequalis*); somewhat resistant to apple mildew (*Podosphaera leucotricha*).

I claim:

1. A new and distinct apple tree named 'PremA025', substantially as described and illustrated herein.

* * * * *